United States Patent [19]
Holmberg

[11] Patent Number: 5,496,296
[45] Date of Patent: Mar. 5, 1996

[54] OSTOMY APPLIANCE WITH EXTRUDABLE GASKET

[75] Inventor: Steen Holmberg, Espergaerde, Denmark

[73] Assignee: Dansac A/S, Fredensborg, Denmark

[21] Appl. No.: 254,503

[22] Filed: Jun. 6, 1994

[51] Int. Cl.⁶ ........................................... A61F 5/44
[52] U.S. Cl. ........................................ 604/336; 604/344
[58] Field of Search ............................. 604/332–344

[56] References Cited

U.S. PATENT DOCUMENTS

| | | | |
|---|---|---|---|
| 3,339,546 | 9/1967 | Chen | 128/156 |
| 3,898,990 | 8/1975 | Nolan | 128/283 |
| 4,477,325 | 10/1984 | Osburn | 204/159.12 |
| 4,538,603 | 9/1985 | Pawelchak et al. | 128/156 |
| 4,738,257 | 6/1988 | Meyer et al. | 128/156 |
| 4,867,748 | 9/1989 | Samuelsen | 604/336 |
| 4,909,244 | 3/1990 | Quarfoot et al. | 128/156 |
| 5,004,464 | 4/1991 | Leise, Jr. | 604/344 |
| 5,074,852 | 12/1991 | Castellana et al. | 604/336 |
| 5,115,801 | 5/1992 | Cartmell et al. | 602/48 |
| 5,147,340 | 9/1992 | Lavender | 604/344 |

*Primary Examiner*—Randall L. Green
*Assistant Examiner*—Rob Clarke
*Attorney, Agent, or Firm*—Tilton Fallon Lungmus

[57] ABSTRACT

An ostomy appliance of one-piece or two-piece construction having an adhesive faceplate with a stoma-receiving opening for peristomal adhesive attachment of the appliance to a wearer. The faceplate includes a flexible patch which may be formed of non-woven material and is covered on one side with a first layer of pressure-sensitive adhesive material—particularly a skinfriendly, tacky, hydrocolloid-containing, moisture-absorbing skin barrier material—surrounding the stoma-receiving opening, and a second layer of a soft, easily-deformable, and extrudable fluid-resistant sealant material also surrounding that opening. Inward displacement of the sealant material following adhesive attachment of the faceplate to a patient results in the formation in situ of a fluid-resistant gasket that prevents stomal fluids from contacting the peristomal skin surfaces and the first layer of skinfriendly adhesive and possibly dissolving that layer and/or disrupting its attachment to the skin.

11 Claims, 2 Drawing Sheets

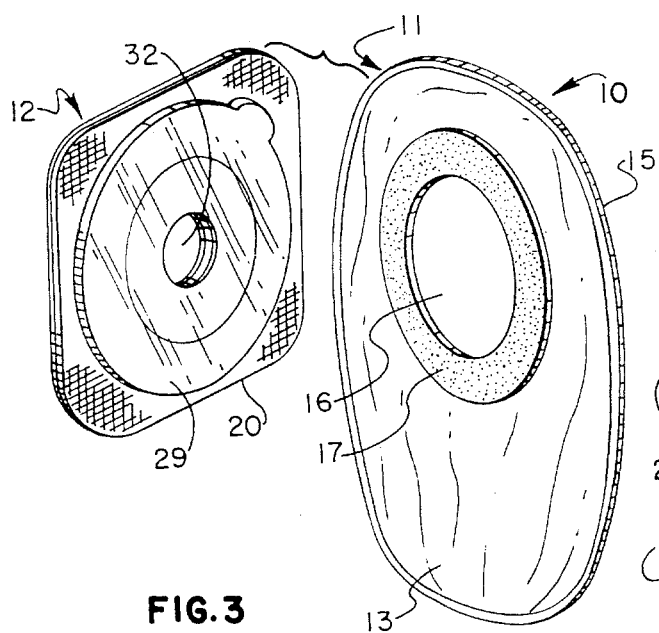
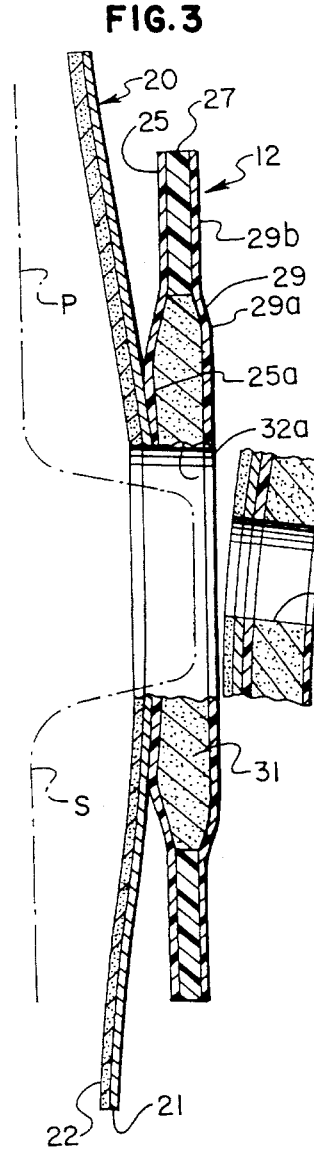
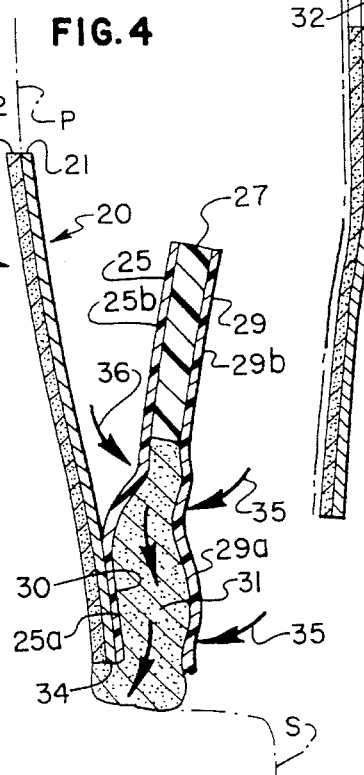
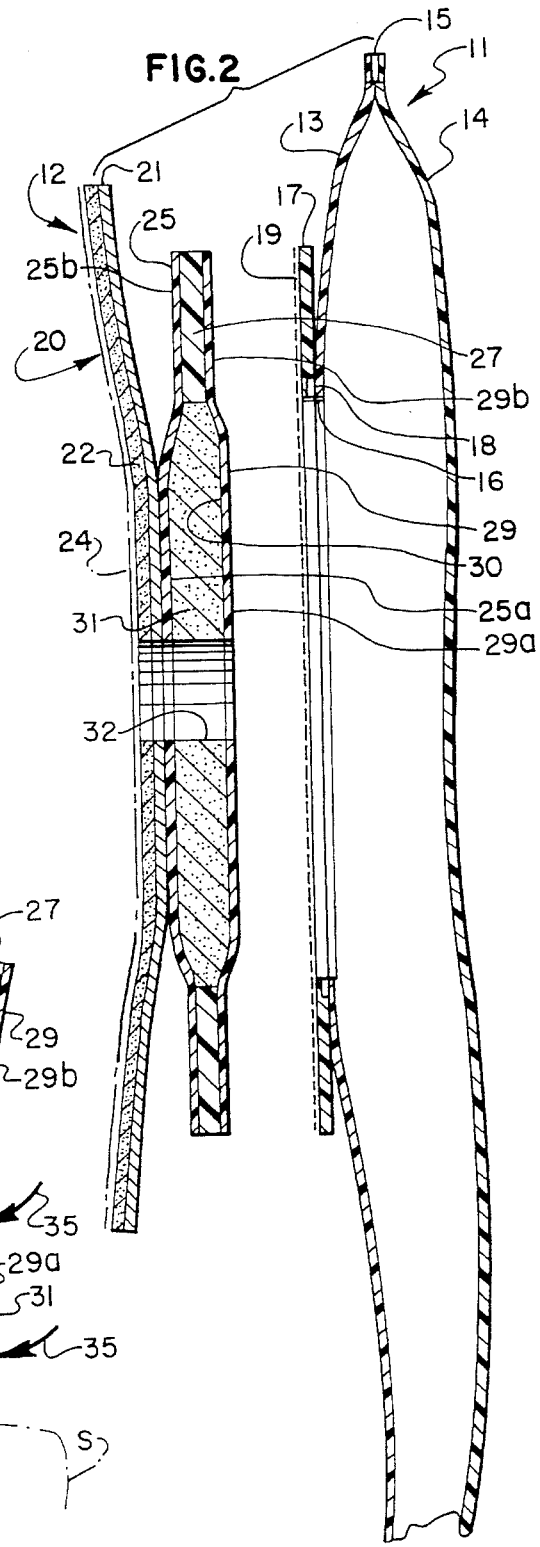

OSTOMY APPLIANCE WITH EXTRUDABLE GASKET

BACKGROUND AND SUMMARY

Ostomy appliances of so-called one-piece and two-piece constructins are commonly provided with adhesive faceplates for adhesively securing the appliances to the peristomal skin surfaces of wearers. While medical grade pressure-sensitive adhesives, usually acrylic adhesives, have been used in the past, recent products have utilized moisture-absorbing, hydrocolloid-containing skin barrier materials for adhesive attachment of faceplates. Such materials are considered "skinfriendly" because they are generally non-allergenic, absorb moisture from the skin and, following a normal interval of use, are of sufficiently reduced tackiness that may be easily peeled away without damaging or irritating the skin.

One skinfriendly adhesive barrier material is disclosed in U.S. Pat. No. 3,339,546 and consists of a blend of a water-soluble and swellable hydrocolloids such as polyvinyl alcohol, powdered pectin, gelatin or carboxymethylcellulose, and a water-insoluble viscous gum-like elastic binder such as natural rubber, silicone rubber, polyurethane rubber, or (notably) polyisobutylene. Tackifiers and plasticizers may be included to vary the properties of such compositions.

In such hydrocolloid-containing barrier compositions, the elastomer constitutes a continuous phase and the hydrocolloid or hydrocolloids are dispersed therein in particulate form. As the hydrocolloids absorb moisture, such a composition swells and begins to lose its integrity. Steps may be taken to retard or prevent barrier disintegration or dissolution, such as by incorporating a polymer capable of being cross-linked by irradiation (see U.S. Pat. Nos. 4,477,325 and 4,738,257). Other barrier compositions that resist disintegration/dissolution have been formulated in which the continuous phase includes a physically cross-linked elastomer consisting of one or more styrene-olefin-styrene block copolymers, a hydrocarbon tackifier resin, and an antioxidant, and a disperse phase consisting of one or more water-swellable hydrocolloids (see U.S. Pat. No. 4,867,748).

One aspect of this invention lies in the observation that the properties which make a barrier material skinfriendly for use in an ostomy appliance, such as ease of removability without skin damage following an interval of use, tend to be compromised to a greater or lesser extent when the composition is formulated to resist dissolution or disintegration upon hydration. On the other hand, it is important that the barrier material of an ostomy appliance function as an effective sealant to prevent leakage of stomal fluids and to protect the peristomal skin surfaces from the aggressive action of such enzyme-containing fluids.

The present invention addresses these problems by providing an ostomy appliance in which the faceplate assembly includes two layers of hydrocolloid-containing adhesive barrier materials of different compositions. The first or primary layer secures the faceplate to the peristomal skin surfaces and is composed of a skinfriendly hydrocolloid-containing barrier material that has relatively low resistance to dissolving and/or disintegrating when contacted by stomal fluids. The second layer directly surrounds the stomal opening of the faceplate and is composed of a relatively soft, easily-deformable and extrudable, adhesive sealant material that is more resistant to dissolution or disintegration by stomal fluids than the material of the first layer. The soft, moldable sealant material may therefore be extruded or displaced inwardly and axially by finger pressure, following initial attachment of a faceplate by means by the first skinfriendly hydrocolloid layer, to form a stoma-contacting gasket that prevents stomal fluids from attacking the peristomal skin surfaces and from reaching and/or dissolving/disintegrating the primary adhesive layer.

Such an arrangement and its use also tends to protect the stoma against direct contact with the inner edges of the patch material (preferably a microporous non-woven material) of the faceplate about its stoma-receiving opening, as well as the edges that define the stoma-receiving opening of the pouch.

Other features, objects, and advantages of the invention will become apparent from the description and drawings.

DRAWINGS

FIG. 1 is a perspective view of a two-piece ostomy appliance embodying the present invention, the appliance being shown with its components in separated condition.

FIG. 2 is an enlarged, somewhat schematic, vertical sectional view of the appliance depicted in FIG. 1.

FIG. 3 depicts the faceplate assembly of the appliance from the size of its stoma-receiving opening that has been increased to accommodate a patient's stoma.

FIG. 4 is an enlarged fragmentary sectional view schematically showing the faceplate assembly after it has been adhered to a patient and forces are applied to displace the moldable sealant material inwardly into sealing contact with the stoma and the skin surfaces immediately surrounding it.

DETAILED DESCRIPTION OF PREFERRED EMBODIMENTS

Figure 5:
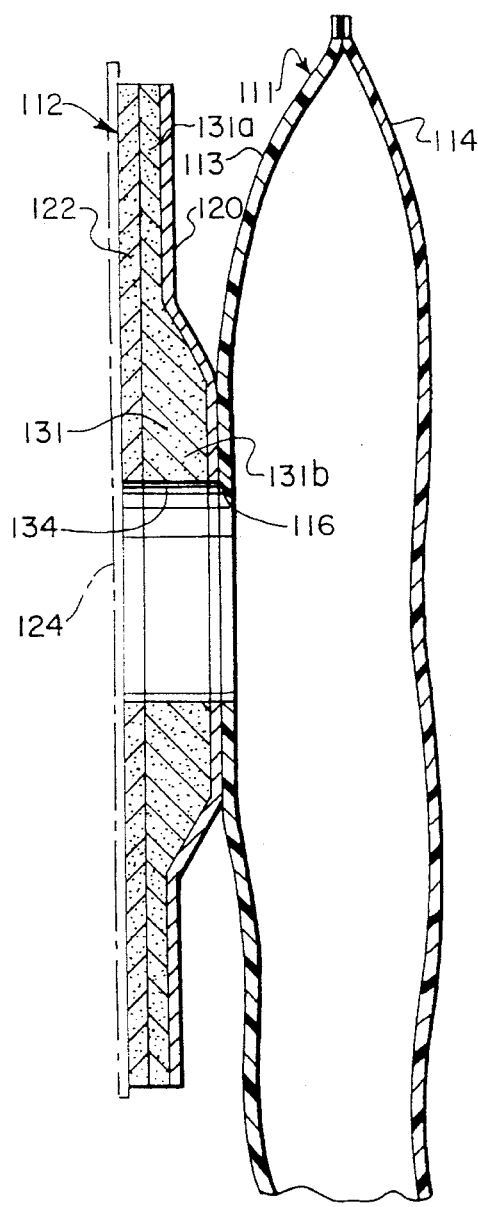
FIG. 5 is a somewhat schematic vertical sectional view of an appliance constituting a second embodiment of the present invention.

Referring to FIGS. 1 and 2, the numeral 10 generally designates an ostomy appliance comprising a pouch 11 and a faceplate assembly 12. The drawings depict a two-piece appliance in which the pouch and faceplate assembly are separable, permitting a series of pouches to be succcessively secured to a faceplate assembly while that assembly remains attached to a patient. It is to be understood, however, that the advantages of the invention may also be achieved, although perhaps to a lesser extent, by an appliance of one-piece construction, that is, a construction in which the pouch and faceplate assembly are permanently connected together. Also, while the two-piece assembly disclosed herein utilizes adhesive coupling of the parts, other types of couplings well known in the art (e.g., mechanical couplings) may be used.

Pouch 11 has a pair of side walls 13 and 14 formed of any suitable, thin, flexible, gas and liquid impermeable polymeric material. Low-density polyethylene coextruded with an odor barrier core material such as polyvinylidene chloride has been found particularly effective. The two walls have their outer periphery heat sealed together at 15, and one of the walls 13 has a stoma-receiving side opening 16. An attachment ring 17 has its inner edge portion heat sealed at 18 to pouch wall 13 about opening 16. The attachment ring may be formed of polyethylene, but of a density and thickness that make it relatively stiff and wrinkle-resistant in contrast to the material of the pouch wall. Other polymeric materials having similar properties may be used. The bodyside surface of the attachment ring is coated with a layer of pressure-sensitive adhesive 19, such as a conventional medical-grade acrylic adhesive. Prior to use, the adhesive surface is covered by a removable release sheet of siliconized paper or other suitable material (not shown), all as well known in the art.

Faceplate assembly 12 includes a flexible patch 20 for securing the appliance to a patient's skin. The patch preferably comprises a sheet 21 of non-woven microporous material having a first adhesive layer 22 along its bodyside surface. Layer 22 is composed of a skinfriendly moisture-absorbing hydrocolloid-containing adhesive having both wet and dry tack. A variety of such barrier-type adhesives are known in the art and may be used here, one such formulation being disclosed, for example, in U.S. Pat. No. 3,339,546. The barrier composition of that patent is gel-forming and loses its integrity in contact with stomal fluid but, as previously noted, the more skinfriendly barrier materials are those which are more likely to dissolve or disintegrate when exposed to such fluid. While layer 22 may be formed of any of variety of known barrier materials less susceptible to such dissolution/disintegration, it is preferred that a more skin-friendly but dissolvable/disintegratable material be used for the primary layer because of the added protective effect provided by a second adhesive layer described below.

The exposed surface of adhesive layer 20 may be covered by a removable release sheet 24, shown in phantom in FIG. 2, to protect that adhesive layer until the time of use.

Referring to FIGS. 2–4, it will be observed that a first annular film or web 25 has its inner portion 25a heat sealed or otherwise permanently secured to the microporous layer of patch 20. The outer portion 25b of the annular film 25 is sealed to a relatively stiff flange ring 27. It will be noted that the inner diameter of the flange ring is substantially greater than the outer diameter of the zone of attachment between inner portion 25a and patch 20.

A second annular film 29 is concentric with the first annular film 25 and has its outer portion 29b sealed to the pouchside surface of flange ring 27. In the illustration given, the entire pouchside surface of the flange ring is covered by film 29 although, if desired, only an inner portion of that surface may be so covered. Of particular importance is the fact that the inner annular portion 29a of the second film 29 is spaced axially from the corresponding inner portion 25a of film 25 to define an annular chamber 30 that contains a second layer 31 of adhesive material.

Adhesive material 31 is formulated to resist dissolution or disintegration by stomal fluids. It should be relatively soft and easily deformable and extrudable by finger pressure. It should also be fluid-absorbing, skinfriendly, and capable of adhering to dry and moist skin surfaces. While a variety of hydrocolloid-containing barrier materials having such properties are known in the art and may be adapted for use herein, a formulation believed to be particularly effective comprises one or more physically cross-linked elastomers forming a continuous phase with one or more hydrocolloids dispersed therein. A preferred elastomer in the continuous phase may be selected from the class identified as styrene-olefin-styrene block copolymers such as a styrene-isopyrene-styrene block copolymer or a styrene-butadiene-styrene block copolymer. A particularly effective formulation is believed to be as follows:

| | |
|---|---|
| Polyisobutylene | 31% (by weight) |
| Styrene-isopyrene-styrene block copolymer (Cariflex 1107S, Shell Chemical Co.) | 5% |
| Karaya powder | 22% |
| Guar gum | 15% |
| Pectin | 9% |
| Paraffin oil | 18% |

A central stoma-receiving opening 32 extends through the entire faceplate assembly as shown clearly in FIGS. 1 and 2. Such opening is a composite of successive concentric openings of equal size in patch 20, first adhesive layer 22, second adhesive layer 31, and films 25 and 29. While opening 32 may be pre-sized during manufacture to accommodate a stoma of any given size, it is preferred that the opening may be relatively small and serve as a starter opening which may then be enlarged prior to application to suit the size of the patient's stoma. Thus, as illustrated in FIG. 3, a patient P having a stoma S of given size may cut the faceplate 12 to provide an enlarged opening 32a of a size sufficiently greater than stoma S that there is no risk of the edges of patch 20 or films 25 and 29 directly contacting the stoma when the faceplate is secured to the peristomal skin surfaces.

The films or webs 25 and 29 are thin and highly flexible whereas flange ring 27 is relatively stiff. As a result, the pouchside surface of the flange ring, or the portion 29b of film 29 that covers that surface, tends to assume a planar condition and provides a smooth non-wrinkling surface for adhesive attachment of the adhesive ring 17 of pouch 11. Such attachment is facilitated by the highly flexible character of the thin films 25 and 29 which support the flange ring for limited floating action. A user may easily insert his/her fingers between patch 20 and the annular film or web 25 to brace the flange ring during a coupling operation. Conversely, forces applied to patch 12 that cause such patch to flex and deform may not be transmitted directly to the flange ring because of the floating action produced by webs 25 and 29.

Referring to FIGS. 3 and 4, since stoma-receiving opening 32a is substantially larger than stoma S, annular spacing 34 (FIG. 4) is formed between the inner edges of patch 20 and annular films 25 and 29 on one hand and the outer surface of stoma S on the other, when the faceplate is adhered to the peristomal skin surfaces of the patient. However, by applying finger pressure to the faceplate as indicated by arrows 35 and 36 in FIG. 4, some of the soft sealant material 31 in the chamber or cavity 30 may be displaced radially inwardly and axially to surround the stoma and fill gap 34. Sealant material conforms to the outer surface of the stoma and protects it against fluid contact when the appliance is in use. Moreover, the extruded sealant material flows inwardly against the peristomal skin surfaces at the stomal root and also seals the edges of microporous layer 21 and the first hydrocolloid-containing layer 22. The sealant material therefore prevents stomal fluids from reaching and dissolving the skinfriendly hydrocolloid-containing adhesive layer 22.

The floating support for flange 27 also plays a role in the extrusion process because cavity 30 extends radially outwardly beyond the attachment of film 25 to patch 20 and, therefore, a user may insert his/her fingers between patch 20 and film 25 to exert a squeezing and adhesive-extruding force in the direction of arrow 36.

Figure 6:
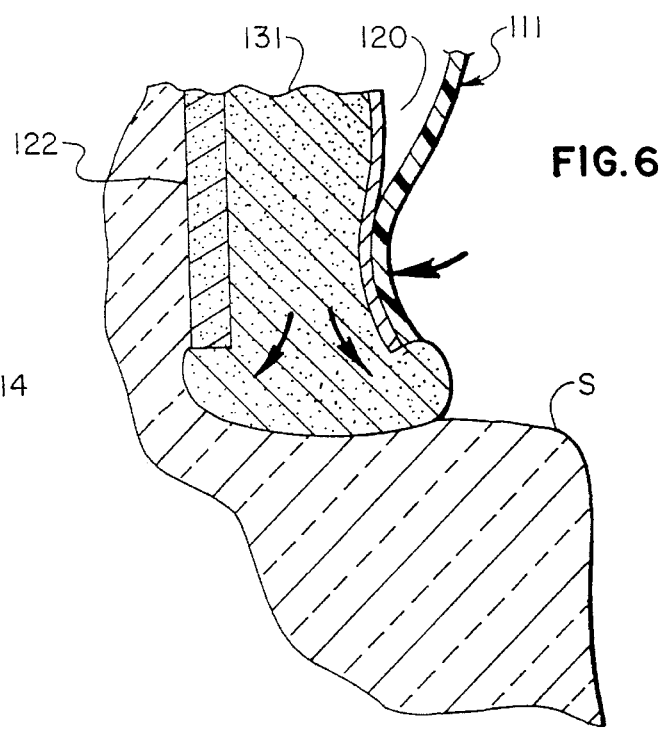
FIG. 6 is an enlarged fragmentary sectional view illustrating the displacement or extrusion of sealant material after initial adhesive attachment of the appliance of FIG. 5 to peristomal skin surfaces.

FIGS. 5 and 6 illustrate a second preferred embodiment in which faceplate assembly 112 is of somewhat simpler construction. That assembly is shown permanently connected to a pouch 111 about the stoma opening 116 formed in wall 113 of that pouch. Instead of being permanently connected, however, the two main components 111, 112 may be detachably joined by adhesive or mechanical coupling means, all as well known in the art. Thus, the faceplate assembly 112 is shown as part of a one-piece appliance but, with the utilization of suitable coupling means, such faceplate assembly may alternatively be used as part of a two-piece appliance.

Faceplate assembly 112 includes a flexible patch 120 preferably formed of non-woven microporous sheet material, a first or primary adhesive layer 122, and a second extrudable adhesive layer 131. A stoma-receiving opening 134 extends through all three layers of the faceplate assembly and is aligned with opening 116 of pouch 111. Opening 134 is substantially larger in diameter than the stoma of the patient to be fitted with the appliance, either because the appliance has been manufactured with an enlarged opening 134 or because at the time of application a user has enlarged a starter opening so that the final opening 134 is properly dimensioned for the particular patient. As in the first embodiment, the bodyside surface of the faceplate assembly may be covered with a removable release sheet 124 (shown in phantom) which would be peeled away to expose the surface of the primary adhesive layer 122 at the time of application.

The first and second adhesive layers 122 and 131 may be identical in composition to layers 22 and 31 of the preceding embodiment. First layer 122 is of hydrocolloid-containing barrier material which is skinfriendly and may be, as a result, susceptible to dissolution or disintegration when exposed to stomal fluid. In any event, the second adhesive layer 131 is composed of a soft, easily-deformable and extrudable, adhesive sealant material that is resistant to becoming dissolved or disintegrated by stomal fluid and is displaceable inwardly and axially into stoma-receiving openings 134 and 116 to form a stoma-engaging gasket that prevents stomal fluids from contacting the outer surface of stoma S and the peristomal surfaces at the foot of the stoma. The gasket also flows inwardly and axially to protect the inner edge of the opening in the first adhesive layer 122 against contact with stomal fluid. The inward and axial displacement of the soft sealant material 131 is achieved simply by applying finger pressure inwardly in the direction of arrow 135 as illustrated in FIG. 6.

The inwardly-displaced annulus of sealant material also protects stoma S against direct contact with the edges of patch 120 and pouch films 113 and 114 that surround the stoma.

Adhesive layers 122 and 131 are coextensive in their radial dimensions but, while layer 122 is preferably of uniform thickness, layer 131 is contoured, having a relatively thin outer flange portion 131a and a relatively thick annular inner portion 131b (FIG. 5). Such contouring may be effectively achieved by the method disclosed and claimed in Jensen U.S. Pat. No. 5,133,821, the disclosure of which is incorporated by reference herein. Most advantageously, the flange portion 131a of layer 131, and layer 122 adjacent thereto, have a combined uniform thickness no greater than about 0.5 mm and a radial dimension of at least 5.0 mm. The relatively thick annular inner portion 131b may be of any desired thickness well in excess of 5.0 mm to provide a sufficient amount of displacable sealant material for forming a sealant gasket in situ as described above.

Figure 7:
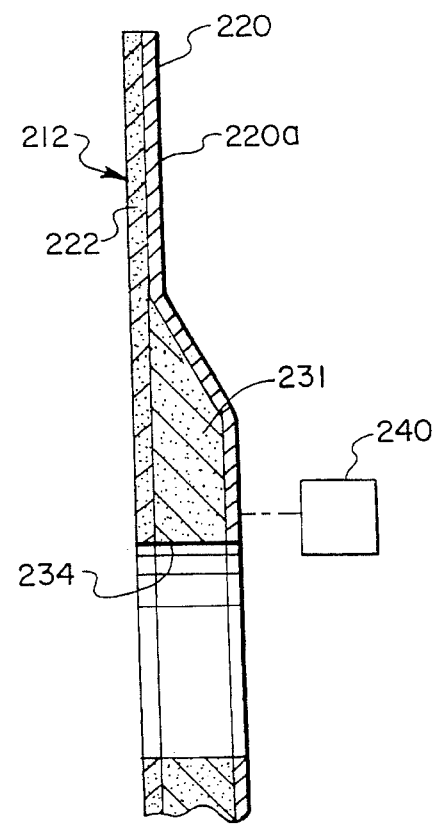
FIG. 7 is a somewhat schematic sectional view of a faceplate for a two-piece appliance constituting a third embodiment of this invention.

The embodiment of FIG. 7 is similar to that of FIG. 5 except that faceplate assembly 212 does not have its second adhesive layer 231 coextensive in planar area with first adhesive layer 222. Microporous non-woven layer 220 therefore has its outer peripheral portion 220a in direct contact with the first adhesive layer 122. Again, the faceplate assembly is contoured with the gasket-forming sealant layer 231 being relatively thick in the area immediately surrounding stoma-receiving opening 234. To prevent channeling and leakage when the appliance is in use, the thin outer flange portion of the first adhesive layer 222 that extends outwardly beyond layer 231 should have a generally uniform thickness no greater than about 0.5 mm and a radial width no less than 5.0 mm.

The embodiment of FIG. 7 also differs from that of FIG. 5 in that faceplate assembly is not permanently secured to a pouch but is instead provided with suitable attachment means 240, diagramatically illustrated in FIG. 7, for adhesive or mechanical attachment to a pouch by coupling systems well known in the art. It is to be understood, of course, that the faceplate assembly of FIG. 7 may, if desired, be permanently secured to a pouch in the same manner as depicted in FIG. 5 and, conversely, that the faceplate assembly 112 of FIG. 5 may be adapted for detachable connection to a pouch as indicated with respect to the embodiment of FIG. 7, or as shown and described with respect to the embodiment of FIGS. 1–4.

While in the foregoing, I have disclosed an embodiment of the invention in considerable detail for purposes of illustration, it will be understood by those skilled in the art that many of these details may be varied without departing from the spirit and scope of the invention.

I claim:

1. An ostomy appliance comprising a collection pouch and faceplate assembly; said faceplate assembly including a flexible patch having a stoma-receiving opening, a first layer of skinfriendly hydrocolloid-containing adhesive material along one side of said patch about said opening for securing said faceplate assembly to peristomal skin surfaces, and a second layer of adhesive sealant material immediately surrounding said opening; said adhesive sealant material of said second layer being softer more easily deformable and extrudable, and more resistant to being dissolved or disintegrated by stomal fluids than the skinfriendly hydrocolloid-containing adhesive material of said first layer and being displacable inwardly and axially into said opening for forming a stoma-engaging annular gasket to prevent stomal fluids from contacting said first adhesive layer.

2. The appliance of claim 1 in which said adhesive material of said second layer includes a continuous phase containing a physically cross-linked or irradition cross-linked polymer and one or more hydrocolloids in particulate form dispersed in said continuous phase.

3. The appliance of claims 1 or 2 in which said flexible patch is formed of microporous sheet material.

4. The appliance of claims 1 or 2 in which said first and second layers are in direct planar contact with each other.

5. The appliance of claim 4 in which said faceplate assembly is contoured and has a relatively thick annular inner portion of adhesive material and a relatively thin annular outer flange portion of adhesive material; said relatively thick annular inner portion being composed of both said first adhesive layer and said second adhesive layer.

6. The appliance of claim 5 in which said outer annular flange portion of adhesive material is composed substantially entirely of said first adhesive layer.

7. The appliance of claims 1 or 2 in which said appliance is a one-piece appliance with said pouch and faceplate permanently connected together.

8. The appliance of claims 1 or 2 in which said appliance is a two-piece appliance with said pouch and faceplate being detachably connected together.

9. An ostomy appliance comprising a collection pouch and faceplate assembly; said faceplate assembly including a flexible patch having a stoma-receiving opening, a first layer of skinfriendly hydrocolloid-containing adhesive material along one side of said patch about said opening for securing said faceplate assembly to peristomal skin surfaces, and a second layer of relatively soft, easily-deformable and extrudable, adhesive sealant material of a composition that is resistant to being dissolved or disintegrated by stomal fluids and that immediately surrounds said opening; said second layer being displacable inwardly and axially into said opening for forming a stoma-engaging annular gasket to prevent stomal fluids from contacting said first adhesive layer; said first and second layers being in direct planar contact with each other; said faceplate assembly being contoured and having a relatively thick annular inner portion of adhesive material and a relatively thin annular outer flange portion of adhesive material; said relatively thick annular inner portion and said annular outer flange portion being composed of both of said first adhesive layer and said second adhesive layer.

10. An ostomy appliance comprising a collection pouch and faceplate assembly; said faceplate assembly including a flexible patch having a stoma-receiving opening, a first layer of skinfriendly hydrocolloid-containing adhesive material along one side of said patch about said opening for securing said faceplate assembly to peristomal skin surfaces, and a second layer of relatively soft, easily-deformable and extrudable, adhesive sealant material of a composition that is resistant to being dissolved or disintegrated by stomal fluids and that immediately surrounds said opening; said second layer being displacable inwardly and axially into said opening for forming a stoma-engaging annular gasket to prevent stomal fluids from contacting said first adhesive layer; said appliance being a two-piece appliance with said pouch and faceplate being detachably connected together; said second adhesive layer having opposite faces covered by first and second films of thin, flexible material; said films each having concentric inner and outer portions with said inner portion of one of said films being secured to said patch adjacent said opening; said one film having its outer portion unsecured to said patch to permit the outer portions of said films to be squeezed together between a user's fingers for extruding said sealant material of said second adhesive layer into said stoma opening.

11. The appliance of claim 10 in which a relatively stiff flange ring is secured to said outer portions of said films; said pouch being provided with an adhesive attachment ring for detachable connection to that part of said faceplate assembly providing said stiff flange ring.

* * * * *